United States Patent [19]

Dobrotvorsky et al.

[11] Patent Number: 5,534,262
[45] Date of Patent: Jul. 9, 1996

[54] PHARMACEUTICAL GRANULATED COMPOSITION AND METHOD FOR PREPARING SAME

[76] Inventors: Anatoly E. Dobrotvorsky, ulitsa Nizhegorodskaya, 5, kv. 133; Yaroslav A. Rozputnyak, ulitsa akademika Yangelya, 8, kv. 102, both of Moscow; Galina N. Khuchua, p/o Mosrentgen, 2, kv. 34, Moskovskaya oblast, Vidnoe-4; Irina A. Komissarova, ulitsa Medkov, 24, kv. 47, Moscow, all of Russian Federation

[21] Appl. No.: 119,049

[22] PCT Filed: Jan. 10, 1992

[86] PCT No.: PCT/RU92/00004

§ 371 Date: Sep. 10, 1993

§ 102(e) Date: Sep. 10, 1993

[87] PCT Pub. No.: WO93/13756

PCT Pub. Date: Jul. 22, 1993

[51] Int. Cl.$^6$ .............................. A61K 9/16; A61K 9/20; A61K 31/195
[52] U.S. Cl. .......... 424/464; 424/465; 424/489; 514/772.3; 514/778; 514/781; 514/784; 514/960; 514/961
[58] Field of Search .................. 424/464, 465, 424/494, 497, 489

[56] References Cited

U.S. PATENT DOCUMENTS

| | | | |
|---|---|---|---|
| 3,063,900 | 11/1962 | Winsor | 167/65 |
| 4,036,948 | 7/1977 | Kitamori et al. | 424/32 |
| 4,465,660 | 8/1984 | David et al. | 424/15 |
| 4,486,455 | 12/1984 | Wolf et al. | 426/548 |
| 4,702,919 | 10/1987 | Kitamori et al. | 424/480 |
| 4,748,023 | 5/1988 | Tamás et al. | 424/465 |
| 4,973,470 | 11/1990 | Mills | 424/467 |

FOREIGN PATENT DOCUMENTS 0219276   4/1987   European Pat. Off. .

Primary Examiner—Thurman K. Page
Assistant Examiner—James M. Spear
Attorney, Agent, or Firm—Ladas & Parry

[57] ABSTRACT

A granulated composition for direct tableting, comprising non-pressed or difficulty pressed, water-soluble, crystalline pharmaceutical substances, binder, lubricant and water, contains at least 98 wt. % of a pharmaceutically active component. The tablets manufactured from said composition have high hardness and the controllable time of dissolution. A method for preparing said composition consists in that the powder of a pharmaceutical substance is pre-granulated with water or its aqueous solution, the resultant granulate is then subjected to subsequent granulation with a binder solution, dried and powdered with lubricant.

12 Claims, No Drawings

PHARMACEUTICAL GRANULATED COMPOSITION AND METHOD FOR PREPARING SAME

TECHNICAL FIELD

This application is a 371 of PCT/RU92/00004, filed Jan. 10, 1992. The present invention relates to the technology of medicaments—to be more exact—to new granulated compositions well tabletted and containing water-soluble, non-pressed and/or difficulty pressed, crystalline pharmaceutical substances, and a method for producing same.

PRIOR ART

Known in the art are granulated compositions intended for tabletting and containing water-soluble, non-pressed and/or difficulty pressed, crystalline pharmaceutical components in which an amount of auxiliary substances reaches 40–90% by weight (EP 342106, EP I08218).

However, a high content of auxiliary ingredients in said compositions reduces bioaccessibility of pharmacological components and considerably changes their pharmacokinetics. Besides, introduction of large amounts of auxiliary substances into pharmaceutical compositions brings about significant power consumption and material expenditures.

Known is a method of producing granulated pharmaceutical compositions (Remington's pharmaceutical sciences, 17-th edition, 1985, Mack publishing company, Eastern Pennsylvania, pp. 16I0-1612).

According to said method, the pharmaceutical compositions are prepared by granulating a powder of pharmaceutical substance with a solution of binding agent in an air-fluidized bed apparatus, by drying the resultant granulate and by sequentially powdering same with a lubricating agent. However, this method does not permit obtaining the granulated compositions containing water-soluble, non-pressed and/or difficulty pressed crystalline pharmaceutical compositions with a minimum of the contained auxiliary substances.

ESSENCE OF THE INVENTION

The claimed granulated composition and method of its production are new and not described in literature.

It is the principal object of the present invention to create a new granulated composition, well tabletted and containing water-soluble, non-pressed and/or difficulty pressed, crystalline pharmaceutical components with a minimal content of auxiliary substances and to elaborate a method of its preparation.

Said object is solved owing to the fact that the claimed granulated composition of the invention comprises following components:

a) a pharmaceutically active agent in an amount of between 96.0 and 98.0% by weight, as calculated for the total final composition;

b) a pharmaceutically acceptable binder in an effective amount of from 0.5 to 2.0% by weight;

c) a pharmaceutically acceptable lubricating agent in an effective amount of from 0.5 to 1.0% by weight;

d) water in an effective amount of from 1 to 3% by weight.

The claimed granulated composition comprises a minimum of auxiliary substances, which secures a maximal bioaccessibility of pharmacologically active components and the most favourable pharmacokinetics thereof. Besides this, the claimed granulated composition is well tabletted (pressed into tablets), the tablets possessing the required strength and the controlled time of dissolution, a factor that enables one to avoid the locally irritating effect of pharmacological active components.

The method of obtaining the claimed granulated composition of the invention includes following stages:

a) pre-granulating of the powder of a pharmaceutical substance with water or its concentrated solution in water. It is advantageous to use the powder of said pharmaceutical substance with a particle size of main fractions not exceeding about 0.3 mm. Said pre-granulation is preferably conducted in an air-fluidized bed apparatus;

b) the subsequent granulation of the resulting granulate (pre-prepared) of a pharmaceutical substance with a solution of binder in water or an organic solvent or a mixture thereof in an air-fluidized bed apparatus;

c) drying the resulting granulate. It is advisable to bring the latter to a moisture content of between 1 and 3% by weight;

d) powdering of the dried granulate with lubricant.

The claimed method of obtaining a granulated composition contributes to improving its plasticity by changing the shape and structure of granules and to reducing the manufacturing cost of the tablets.

PREFERRED EMBODIMENT OF THE INVENTION

The pharmaceutical components (glycine, mannitol and histidine) a binding component—polyvinylpyrrolidone, organic solvents and water meet the quality requirements of the State pharmacopoeia of the USSE; binding components—starch, cellulose esters and also lubricating components, stearic acid and its salts meet the quality requirements of the technical-norm documentation of the USSR.

The powders of pharmaceutical components comprise above 99% of basic substance. The particle size of main fractions of said pharmaceutical component powder does not preferably exceed 0.3 mm which enables one to prepare tablets having a smooth uniform surface which meet requirements of their appearance (The State pharmacopoeia of the USSR, XI, edit.2,pp.154,155).

The binding components may be represented by any pharmaceutically acceptable binders, such as methyl cellulose, hydroxypropyl cellulose, hydroxypropylmethyl cellulose, sodium carboxymethyl cellulose, ethyl cellulose, acetylphthalyl cellulose, polyvinylpyrrolidone, starch, sugars, natural gums, gelatin, dextrins, shellac, pectine, algin derivatives, chitosan.

It is prefered to use cellulose esters, starch and polyvinylpyrrolidone in view of their safety and a wide variety of application in the pharmaceutical industry.

The amount of binder in the claimed composition predetermines the time of dissolving tablets from 0.5 to 2 wt. %, as calculated for the total composition.

The lubricating components used may be represented by any pharmaceutically acceptable lubricants such as stearic acid and salts thereof, polyethylene glycols, hydrogenated vegetable oils, talc, sodium lauryl sulphate or their rational combinations.

It is also preferred to use stearic acid, calcium stearate or magnesium stearate, granule surface waterproofing water-soluble pharmaceutical components. The amount of lubricant is between 0.5 and 1.0 wt. % as calculated for the total composition.

The claimed composition also includes water in an amount necessary for conducting a process of direct tableting, i.e., from 1.0 to 3.0 wt. % as calculated for the total composition.

Thus, the claimed composition of the invention includes said components in the following ratio as calculated in terms of the total weight of the composition.

TABLE I

| Component | Permissible quantity, wt. % |
| --- | --- |
| Pharmaceutical substance | 96.0–98.0 |
| Binding agent | 0.5–2.0 |
| Lubricating agent | 0.5–1.0 |
| Water | 1.0–3.0 |

The optimum make-up of the claimed composition is determined in each concrete case by the nature of a pharmaceutical component and the time of tablet dissolution.

The claimed granulated composition can be subjected to direct pressing into tablets having a strength of from 13 to 138 N (Hardness) and the time of dissolution from one to 55 minutes.

The method of obtaining the claimed composition of the invention is carried out as follows.

The powder of a pharmaceutical substance is subjected to pre-granulation. In order to to more evenly distribute water in the mass of a pharmaceutical component and accelerate the process, it is advantageous to pre-granulate the powder in an air-fluidized bed apparatus.

For this, the estimated quantity of powder of a pharmaceutical component is placed in an air-fluidized bed granulating apparatus and wetted with water or its concentrated solution in water. The obtainable granulate is then dried to a residual moisture content of between 3 and 5 wt. % and subsequently granulated in the same apparatus with a solution of binder in water or an organic solvent or a mixture thereof. The resultant granulate is dried. To assure the most favourable plasticity of the granulate, it is advisable to bring it to a residual moisture content of between 1 and 3 wt. %. The granulate is then taken out of the apparatus per se, screened through a sieve having meshes of 0.5 mm in diameter and powdered with a lubricating agent in a mixer.

the preliminary granulation of powder of a pharmaceutical substance can also be carried out in a granulating machine for wet granulation, for which purpose the calculated quantity of powder is placed in the granulating machine per se, wetted with water or its concentrated solution in water and throroughly stirred up. The granulated mass is then loaded out of the granulating machine, triturated through a sieve having meshes of 1 mm in diameter and dried to a residual moisture content of between 3 and 5 wt. %. The dried granulate is triturated through the sieve having meshes of 0.5 mm in diameter, loaded into an air-fluidized bed apparatus, and the process is further conducted in a way similar to one as described hereinabove.

The final granulated composition is subjected to direct tableting, i.e., with no additional auxiliary substances employed with different pressures expressed in megapascal (MPa): 98.196 and 294.

The strength of tablets is measured on a Erweka Tablet Hardness Tester and expressed in international units of force—newtons, N.

To evaluate tablet dissolution, use is made of $T_{100\%}$ index meaning the time for a pharmaceutical component to completely transit to a solution and expressed in minutes. The definition of value $T_{100\%}$ is preformed according to the State pharmacopoeia of the USSR, XI, edit. 2, pp. 159, 160.

To assess the tablets for abrasion resistance, use is made of an index of loss of their mass in testing as expressed in percentage. Said abrasion resistance is determined in accordance with the State pharmacopoeia of the USSR, XI, edit. 2 pp. 157,158. The tablets manufactured from the claimed composition have a diameter of at least 9 mm and mass of 300 mg.

The present invention is illustrated by following examples.

EXAMPLE 1

292.5 g of glycine powder with a particle size of main fraction of not over 0.2 mm are placed in an apparatus for drying in an air-fluidized bed (Aeromatic AG, Model STREA-I) and granulated in 100 ml of water. The obtainable granulate is then dried to a residual moisture content of 5 wt. % and further granulated in the same apparatus with 150 ml of 2% aqueous solution of methyl cellulose, M - 100. The resultant granulate is dried to a residual moisture content of 1 wt. %, taken out of the apparatus of the air-fluidized bed, screened through a sieve with meshes of 0.5 mm in diameter and powdered with 1.5 g of magnesium stearate in a still mixer (Erweka, Model KB20/UG).

The final granulated composition includes said ingredients in the following ratio, based on the total mass of the composition:

TABLE 2

| Components | Amounts, wt. % |
| --- | --- |
| Glycine | 97.5 |
| Methyl cellulose | 1.0 |
| Magnesium stearate | 0.5 |
| Water | 1.0 |

The granulated composition is subjected to direct tableting on an eccentric press (Erweka, Model EKO). The resulting tablets have physical properties indicated in Table3.

TABLE 3

| Properties | Unit pressure, mPa | | |
| --- | --- | --- | --- |
| | 98 | 196 | 294 |
| Hardness, N | 18 | 35 | 55 |
| Dissolution, $T_{100\%}$ in minutes | 20 | 28 | 30 |
| Abrasion resistance, % | 0.3 | 0.3 | 0.2 |

EXAMPLE 2

292.5 g of glycine powder with a particle size of main fraction is not over 0.2 mm are placed in a laboratory mixer for wet granulation (Erweka, Model SW I/S) and granulated with 90 ml of water. The resulting mass is transferred to the wet granulator (Erweka, Model FGS), triturated through a net having meshes of 1 mm in diameter and dried in a desiccator (B&T "Stabilec" Oven, Model 322/0205) at 60° C. to a residual moisture content of about 5 wt. %. The resultant granulate is placed in an apparatus for drying in an air-fluidized bed (Aeromatic AG, Model STREA-1) and granulated with 300 ml of 1% aqueous solution of methyl cellulose, M-100.

The process is further conducted according to Example 1.

The final granulated composition has a formulation as indicated in Table 2.

The granulated composition is subjected to direct tableting on an eccentric press (Erweka, Model EKO). The obtainable tablets possess physical properties shown in Table 4.

|  | Unit pressure, mPa | | |
| --- | --- | --- | --- |
| Physical properties | 98 | 196 | 294 |
| Hardness, N | 17 | 25 | 33 |
| Dissolution, $T_{100\%}$, minutes | 12 | 18 | 22 |
| Abrasion resistance, % | 0.25 | 0.25 | 0.20 |

EXAMPLE 3

276 g of glycine powder with a particle size of mainfraction of not over 0.2 mm are placed in a laboratory mixer for wet granulation (Erweka, Model SW I/S) and granulated with 90 g of a 20% aqueous solution of glycine. The process is continued according to the run of Example 2 except for the fact that the subsequent granulation in an apparatus of the the air-fluidized bed of a pre-prepared granulate is carried out with 300 ml of a 0.5% aqueous solution of methyl cellulose, M-100.

The final granulated composition includes ingredient in a ratio based on the total mass of the composition:

TABLE 5

| Components | Amounts, wt. % |
| --- | --- |
| Glycine | 98.0 |
| Methyl cellulose | 0.5 |
| Magnesium stearate | 0.5 |
| Water | 1.0 |

The granulated composition is subjected to direct tableting on an eccentric press (Erweka, Model EKO). The resulting tablets have physical properties indicated in Table 6.

TABLE 6

|  | Unit pressure, mPa | | |
| --- | --- | --- | --- |
| Properties | 98 | 196 | 294 |
| Hardness, N | 41 | 64 | 82 |
| Dissolution, $T_{100\%}$, minutes | 9 | 13 | 16 |
| Abrasion resistance, % | 0.1 | 0.2 | 0.2 |

EXAMPLE 4

292.5 g of powder D-mannitol, the firm Chemapol, having a particle size of main fraction of not over 0.2 mm are placed in a laboratory mixer for wet granulation (Erweka, Model SW I/S) and granulated with 100 ml of water. The process is further conducted according to the run of Example 2 except for the fact that the subsequent granulation in an apparatus of the air-fluidized bed of the preliminarily obtainable mannitol granulate is carried out with 150 ml of 1% aqueous solution of starch paste, whereupon the granules are dried to a residual moisture content of 1.5 wt. %, with calcium stearate used as lubricant.

The final granulated composition includes ingredients in a ratio based on the total mass of the composition:

TABLE 7

| Components | Amounts, wt. % |
| --- | --- |
| Mannitol | 97.5 |
| Starch | 0.5 |
| Calcium stearate | 0.5 |
| Water | 1.5 |

The granulated composition is subjected to direct tableting on an eccentric press (Erweka, Model EKO). The resultant tablets have physical properties indicated in Table 8.

TABLE 8

|  | Unit pressure, mPa | | |
| --- | --- | --- | --- |
| Properties | 98 | 196 | 294 |
| Hardness, N | 23 | 56 | 94 |
| Dissolution, $T_{100\%}$, minutes | 22 | 26 | 29 |
| Abrasion resistance, % | 0.1 | 0.15 | 0.25 |

EXAMPLE 5

280.5 g of powder D-mannitol, the firm Chemapol, having a particle size of main fraction of not more than 0.3 mm are placed in an apparatus for drying in an air-fluidized bed (Aeromatic AG, Model STREA-I) and granulated with 75 g of a 10% aqueous mannitol solution. The process is further conducted according to the run of Example 1 except for the fact that the subsequent granulation of the pre-prepared mannitol granulate is carried out with 300 ml of a 2% sodium solution of carboxymethyl cellulose in a solvent of water:ethanol:acetone in a weight ratio of 5:4:1, with stearic acid (3.0 g) utilized as lubricant.

The final granulated composition includes ingredients in a ratio based on the total mass of the composition:

TABLE 9

| Components | Amounts in wt % |
| --- | --- |
| Mannitol | 96.0 |
| Sodium carboxymethyl cellulose | 2.0 |
| Stearic acid | 1.0 |
| Water | 1.0 |

The granulated composition is subjected to direct tableting on an eccentric press (Erweka, Model EKO). The prepared tablets have physical properties indicated in Table 10.

TABLE 10

|  | Unit pressure, mPa | | |
| --- | --- | --- | --- |
| Properties | 98 | 196 | 294 |
| Hardness, N | 66 | 125 | 138 |
| Dissolution, $T_{100\%}$, in minutes | 42 | 48 | 55 |
| Abrasion resistance, % | 0.1 | 0.1 | 0.1 |

EXAMPLE 6

288 g of powder D—histidine of hydrochloride, the firm Sigma, with a particle size of main fraction of at least 0.3 mm are placed in an apparatus for drying in an air-fluidized bed (Aeromatic AG, Model STREA-I) and granulated with 75 g of a 10% aqueous solution of histidine. The process is further conducted in a way similar to Example 1 except for the fact that the subsequent granulation of the pre-prepared histidine granulate is carried out with 300 ml of a 0.5% solution of polyvinylpyrrolidone having a molecular mass of between 12600±2700 in ethanol, by sequentially drying the granulate to a residual moisture content of 3 wt. % and the lubricant used is represented by a mixture of 1 g of calcium stearate with 0.5 g of stearic acid.

The final granulated composition includes ingredients in a ratio based on the total mass of the composition:

TABLE II

| Components | Amounts, wt. % |
|---|---|
| Histidine | 96.00 |
| Polyvinylpyrrolidone | 0.50 |
| Calcium stearate | 0.33 |
| Stearic acid | 0.17 |
| Water | 3.00 |

The granulated composition is subjected to direct tableting on an eccentric press (Erweka, Model EKO), The obtainable tablets have physical properties indicated in Table 12.

TABLE 12

| Properties | Unit pressure, mPa | | |
|---|---|---|---|
|  | 98 | 196 | 294 |
| Hardness, N | 13 | 30 | 50 |
| Dissolution, $T_{100\%}$, in minutes | 1 | 2 | 5 |
| Abrasion resistance, % | 0.3 | 0.3 | 0.2 |

Industrial Applicability

The granulated composition of patent protection sought and a method for its preparation find application in the know-how practice of non-pressed and difficulty pressed, water-soluble crystalline pharmaceutical substances for the production of granulated tabletted medicinal forms.

We claim:

1. A pharmaceutical granulated composition comprising a water soluble pharmaceutical substance selected from the group consisting of glycine, mannitol and histidine, a binder selected from the group consisting of cellulose esters, starch and polyvinylpyrrolidone, a lubricant and water, said pharmaceutical substance, binder, lubricant and water being present in the composition in the following ratio by weight %:

| Pharmaceutical substance | 96.0–98.0 |
|---|---|
| Binder | 0.5–2.0 |
| Lubricant | 0.5–1.0 |
| Water | 1.0–3.0 | and composition having a plasticity sufficient to allow it to be formed into a tablet having a hardness of at least 13N at a tableting pressure of 98 MPa.

2. A composition of claim 1, characterized in that it comprises a binder represented by cellulose esters which are soluble in water or an organic solvent or a mixture thereof.

3. A composition of claim 1, characterised in that it further comprises starch as binder.

4. A composition of claim 1, characterized in that it comprises a binder represented by polyvinylpyrrolidone with a molecular mass of between 12600±2700.

5. A composition of claim 1, characterized in that it comprises a lubricant represented by stearic acid or its pharmaceutically acceptable salts or a mixture thereof.

6. A composition as claimed in claim 1, wherein the composition is produced by a process comprising
   a) pre-granulating a powder of the pharmaceutical substance with water or with a concentrated solution of the pharmaceutical substance in water to form a pregranulate;
   b) granulating the pregranulate with a solution of the binder in an air-fluidized bed to form a resultant granulate, said solution comprising water;
   c) drying the resultant granulate to a moisture content of between about 1–3 weight % and powdering it with the lubricant.

7. A composition as claimed in claim 1, wherein the lubricant is selected from the group consisting of stearic acid and salts thereof, calcium stearate, and magnesium stearate.

8. A composition as claimed in claim 1, wherein the pharmaceutical substance is glycine and the binder is a cellulose ester.

9. A composition as claimed in claim 1, wherein the pharmaceutical substance is mannitol and the binder is a starch.

10. A composition as claimed in claim 1, wherein the pharmaceutical substance is histidine and the binder is polyvinylpyrrolidone.

11. A composition as claimed in claim 8, wherein the composition consists essentially of said pharmaceutical substance, said binder, said lubricant and water.

12. A composition as claimed in claim 11, wherein the binder is present in an amount of about 0.5%.

* * * * *